United States Patent
Barrette et al.

(10) Patent No.: US 6,883,217 B2
(45) Date of Patent: Apr. 26, 2005

(54) APPARATUS FOR DISASSEMBLING MATING TAPER CONNECTIONS

(75) Inventors: John J. Barrette, Warsaw, IN (US); Gregory Meadows, Warsaw, IN (US)

(73) Assignee: Zimmer Technology, Inc., Chicago, IL (US)

(*) Notice: Subject to any disclaimer, the term of this patent is extended or adjusted under 35 U.S.C. 154(b) by 61 days.

(21) Appl. No.: 10/318,854

(22) Filed: Dec. 13, 2002

(65) Prior Publication Data

US 2004/0111861 A1 Jun. 17, 2004

(51) Int. Cl.$^7$ ............... B23P 19/04; B23P 19/00
(52) U.S. Cl. ................................ 29/256; 29/700
(58) Field of Search ............... 29/700, 286, 244, 29/426.5, 426.1, 255; 623/22, 46; 606/105, 62, 57, 90

(56) References Cited

U.S. PATENT DOCUMENTS

| | | | |
|---|---|---|---|
| 4,051,559 A | * 10/1977 | Pifferi | 623/22.46 |
| 5,002,578 A | 3/1991 | Luman | |
| 5,540,687 A | * 7/1996 | Fairley et al. | 606/60 |
| 5,653,765 A | 8/1997 | McTighe et al. | |
| 6,491,696 B1 | * 12/2002 | Kunkel | 606/105 |

OTHER PUBLICATIONS

Brochure—ZMR Revision Taper Hip Prosthesis, Zimmer 1999, 2002, 25 pages.

* cited by examiner

*Primary Examiner*—John C. Hong
(74) *Attorney, Agent, or Firm*—Jonathan Feuchtwang Baker & Daniels

(57) ABSTRACT

A disassembly tool for disassembling components secured together by a mating taper connection. The disassembly tool of the present invention includes a self-tapping sleeve for securement in the longitudinal bore of the component having the female portion of the locking taper connection. The self-tapping sleeve includes self-tapping external threads for securing the self-tapping sleeve in the longitudinal bore of the component having the female taper. The self-tapping sleeve further includes a longitudinal bore having internal threads mating with external threads of a threaded inner rod. In use, the self-tapping sleeve is engaged in the longitudinal bore of the component having the female taper. The threaded inner rod is thereafter threaded through the threaded longitudinal bore in the self-taping sleeve until the distal end of the threaded rod abuts the end of the component having the male taper and forces separation of the locking taper connection.

16 Claims, 1 Drawing Sheet

APPARATUS FOR DISASSEMBLING MATING TAPER CONNECTIONS

BACKGROUND OF THE INVENTION

1. Field of the Invention

The present invention relates to an apparatus for disassembling mating taper connections, and, more particularly to an apparatus for disassembling Morse taper connections in modular prosthetic implants.

2. Description of the Related Art

Mating taper connections can be used for temporarily securing one item to another. One such taper connection is a Morse taper connection. Generally, a Morse taper is defined as a taper connection having a taper surface making an angle of about 2 to 12 degrees relative to the longitudinal axis of the component. Morse taper connections can be made between interpenetrating parts, with, e.g., a first of the parts having a tapered bore, and a second of the parts having a frustoconical shape for securement in the tapered bore of the first part. The tapered bore and the frustoconical shape can have slightly different sizes or taper angles to facilitate securement of the parts via the mating taper connection as described below. To assemble mating taper connections, including Morse taper connections, items having a mating taper structure are interference fit one to the other to cause cointegration or locking of the items. In some cases the cointegration results in material transfer across the zone of contact, i.e., cold welds.

For example, modular femoral implants utilize a Morse taper to secure the proximal body to the distal stem. One such modular femoral implant is the modular femoral implant utilized in the ZMR™ Hip System produced by Zimmer, Inc of Warsaw Indiana. In modular femoral implants, the distal stem generally includes a frustoconical proximal end comprising the male portion of the locking taper, with the longitudinal bore of the proximal body including a mating female taper formed in the distal portion of the longitudinal bore of the proximal body.

A locking taper connection makes a strong connection between two components making disassembly of the components difficult. The present invention is directed to an apparatus for facilitating disassembly of components secured together via a mating taper connection.

SUMMARY OF THE INVENTION

The present invention provides an apparatus for facilitating disassembly of components secured together by a mating taper connection. The apparatus of the present invention is particularly adapted to facilitate separation of interpenetrating parts locked together with a locking taper connection such as a Morse taper. The disassembly tool of the present invention includes a sleeve for securement in the longitudinal bore of the component having the female portion of the locking taper connection. In one embodiment, the component having the female taper is tapped, and the sleeve is thereafter threadedly engaged in the component having the female taper. In another embodiment, the sleeve of the disassembly tool of the present invention includes self-tapping external threads for effecting affixation of the sleeve to the component having the female taper. The sleeve includes a longitudinal bore having internal threads mating with external threads of a threaded inner rod. In use, the sleeve is engaged in the longitudinal bore of the component having the female taper. The threaded inner rod is thereafter threaded through the threaded longitudinal bore in the self-tapping sleeve until the distal end of the threaded rod abuts the end of the component having the male taper. Threading of the inner rod through the self-tapping sleeve continues until the inner rod forces separation of the locking taper connection.

In the case of a modular femoral component, the self-tapping sleeve of the disassembly tool of the present invention engages the proximal body of the modular femoral implant through the longitudinal bore formed therein. The inner rod is then threaded through the self-tapping sleeve until the distal end of the inner rod contacts the proximal end of the distal stem of the modular femoral component. Threading of the inner rod through the self-tapping sleeve continues until the inner rod forces the distal stem out of engagement with the proximal body.

After disassembly of a modular prosthetic femoral component with the apparatus of the present invention, both the proximal body and the distal stem can be readily recognized as used components. The proximal body is recognized as a used component because of the internal threads tapped in the longitudinal bore thereof. The distal stem is recognized as a used component because the force applied by the distal end of the inner rod against the proximal end of the distal stem of the modular prosthetic femoral component marks the proximal end of the distal stem. To facilitate marking the distal stem, the distal end of the inner rod includes a raised feature for producing an indentation on the distal stem when the disassembly apparatus is used to disassemble a modular prosthetic femoral component.

The present invention advantageously facilitates disassembly of a mating taper connection while marking the disassembled components as used components.

BRIEF DESCRIPTION OF THE DRAWINGS

The above-mentioned and other features and advantages of this invention, and the manner of attaining of them, will become more apparent and the invention itself will be better understood by reference to the following description of an embodiment of the invention taken in conjunction with the accompanying drawings, wherein.

Figure 1:
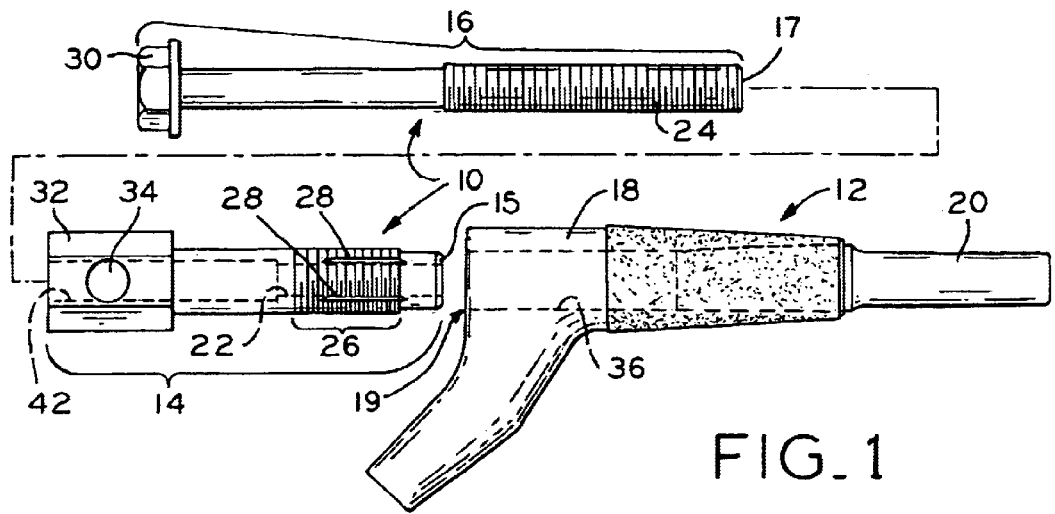
FIG. 1 is a plan view of an assembled modular prosthetic femoral implant together with an exploded view of a disassembly tool of the present invention.

Corresponding reference characters indicate corresponding parts throughout the several views. Although the drawings represent embodiments of the invention, the drawings are not necessarily to scale and certain features may be exaggerated to better illustrate and explain the invention. The exemplifications set out herein illustrate embodiments of the invention, and such exemplifications are not to be construed as limiting the scope of the invention in any manner.

DETAILED DESCRIPTION

Referring to the drawings, and particularly to FIG. 1, there is illustrated disassembly tool 10, including self-tapping sleeve 14, and inner rod 16. Also illustrated in FIG. 1 is assembled modular prosthetic femoral implant 12, including proximal body 18, and distal stem 20.

Figure 2:
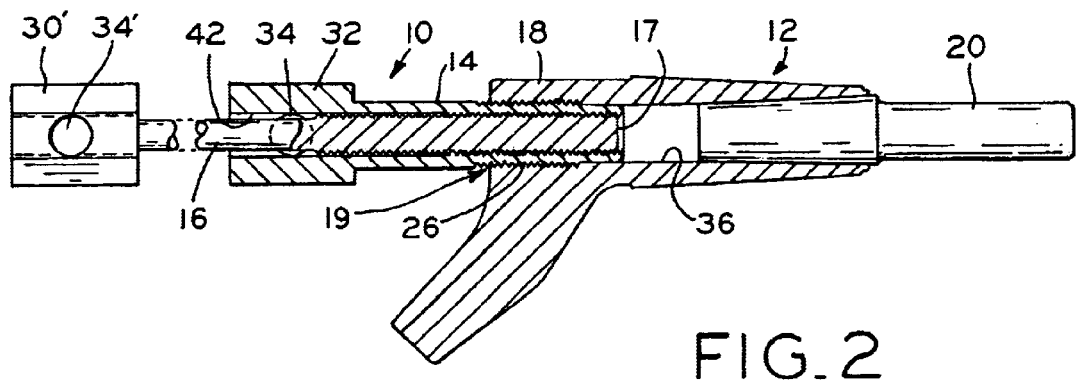
FIG. 2 is a sectional view of the assembled modular prosthetic femoral implant of FIG. 1, illustrating the self-tapping sleeve of the disassembly tool of the present invention secured in the proximal body of the modular prosthetic femoral implant and the inner rod of the disassembly tool of the present invention threadedly engaged with the self-tapping sleeve.
Figure 3:
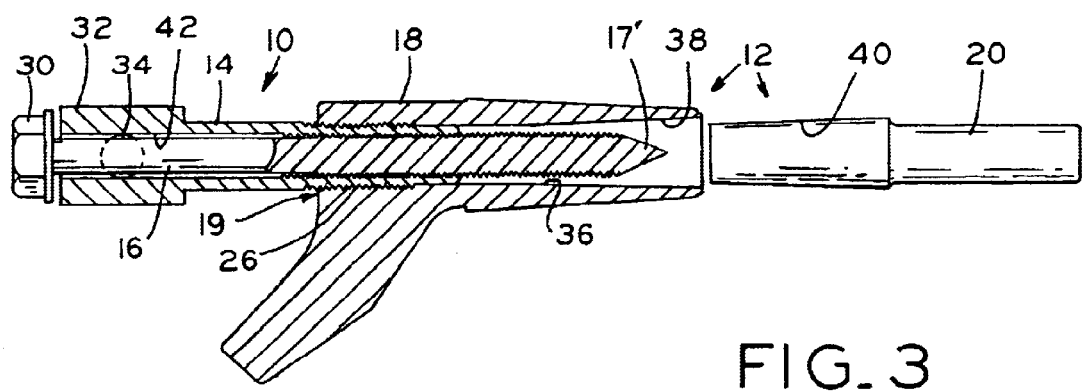
FIG. 3 is a sectional view of a disassembly tool of the present invention engaged with a modular prosthetic femoral component, with the inner rod of the disassembly tool actuated to displace the distal stem of the modular prosthetic femoral component from the proximal body thereof.

As illustrated in FIGS. 1–3, proximal body 18 of modular prosthetic femoral component 12 includes longitudinal bore 36 including female taper 38 (FIG. 3). As illustrated in FIG. 3, female taper 38 of proximal body 18 comprises a frustoconical female taper. As further illustrated in FIGS. 1–3, distal stem 20 of modular prosthetic femoral component 12 includes male taper 40 (FIG. 3) formed on the proximal end thereof. As illustrated, male taper 40 comprises a frustoconical male taper. While illustrated as frustoconical tapers, female taper 38 and male taper 40 may take other forms such as wedge shaped tapers.

FIGS. 1 and 2 illustrate modular prosthetic femoral component 12 in assembled form, with proximal body 18 secured to distal stem 20 via an interference fit of male taper 40 in female taper 38. To disassemble modular prosthetic femoral component 12, self-tapping sleeve 14 is positioned with its longitudinal axis generally aligned with the longitudinal axis of proximal body 18 as illustrated in FIG. 1. Self-tapping sleeve 14 is thereafter secured in longitudinal bore 36 of proximal body 18 as illustrated in FIGS. 2 and 3.

As illustrated in FIG. 1, self-tapping sleeve 14 includes self-tapping external threads 26. Flutes 28 are oriented substantially parallel to the longitudinal axis of proximal body 18 and are formed along a length of self-tapping threads 26. While only two flutes 28 are illustrated in FIG. 1, flutes 28 are generally evenly spaced about the outer diameter of self-tapping sleeve 14. In one exemplary embodiment, self-tapping sleeve 14 includes four flutes 28. Flutes 28 facilitate use of self-tapping external threads 26 to cut threads in, or tap longitudinal bore 36 of proximal body 18. In an alternative embodiment, the external threads of the sleeve of the present invention are not self-tapping, and a discrete tap is used to form threads in longitudinal bore 36 of proximal body 18.

With self-tapping sleeve 14 aligned with proximal body 18 as described above, distal end 15 of self-tapping sleeve 14 is positioned in longitudinal bore 36 until self-tapping threads 26 abut proximal end 19 of proximal body 18. In this position, a tool or handle is connected to self-tapping sleeve 14 to facilitate tapping of longitudinal bore 36. In one exemplary embodiment, a wrench is connected to head 32 of self-tapping sleeve 14 to facilitate rotation thereof to tap longitudinal bore 36. To facilitate connection of a wrench to head 32, head 32 is formed with a generally polygonal cross section. In the embodiment illustrated in FIG. 1, head 32 is formed with a hexagonal cross section. In another exemplary embodiment, a rod is positioned through transverse aperture 34, which is formed through head 32 generally perpendicular to the longitudinal axis of self-tapping sleeve 14. Once a rod is positioned through transverse aperture 34, or a wrench is connected to head 32, force can be applied to the wrench or rod a distance from the longitudinal axis of self-tapping sleeve 14 to supply a torque to self-tapping sleeve 14 and tap longitudinal bore 36 of proximal body 18.

Self-tapping sleeve 14 is advanced into longitudinal bore 36 of proximal body 18, with self-tapping threads 26 tapping longitudinal bore 36 as self-tapping sleeve 14 is advanced into longitudinal bore 36. As described above, tapping of proximal body 18 advantageously marks proximal body 18 as a used component. Self-tapping sleeve 14 is advanced into longitudinal bore 36 until firmly secured therein as illustrated in FIGS. 2 and 3. After self-tapping sleeve 14 is secured to proximal body 18, the wrench or rod utilized to apply torque to self-tapping sleeve 14 is removed and inner rod 16 is positioned through longitudinal bore 42 of self-tapping sleeve 14 until external threads 24 of inner rod 16 meet internal threads 22 (FIG. 1) formed in longitudinal bore 42 of self-tapping sleeve 14. Inner rod 16 is thereafter rotated, with external threads 24 of inner rod 16 cooperating with internal threads 22 of self-tapping sleeve 14 to further advance inner rod 16 through self-tapping sleeve 14. Inner rod 16 is advanced through self-tapping sleeve 14 until distal end 17 of inner rod 16 abuts the proximal end of distal stem 20. Once distal end 17 of inner rod 16 abuts the proximal end of distal stem 20, inner rod 16 is further rotated to advance inner rod 16 through self-tapping sleeve 14 and force distal stem 20 out of its interference fit with proximal body 18 as illustrated in FIG. 3.

As described above, distal end 17 of inner rod 16 includes a raised feature for producing an indentation on distal stem 20 when the disassembly apparatus is used to disassemble modular femoral component 12. This raised feature may take the form of a cup point, or other raised point formed on distal end 17 of inner rod 16. Generally, the raised feature formed on distal end 17 of inner rod 16 comprises a protrusion extending from distal end 17 having a structure designed for marking an end of distal stem 20. In certain embodiments, this structure can take the form of a raised point located anywhere on distal end 17 of inner rod 16. For example, a raised point may be centrally located whereby the apex thereof generally coincides with a longitudinal axis of inner rod 16. In other embodiments, the raised point may be positioned a distance from the longitudinal axis of inner rod 16. These embodiments are particularly useful when disassembling a modular prosthetic implant having a distal stem with a central aperture. When disassembling a modular prosthetic implant having a distal stem with a central aperture, the raised feature on distal end 17 of inner rod 16 will be spaced from the longitudinal axis of inner rod 16 a sufficient distance to contact the proximal end of the distal stem of the modular prosthetic component a distance from the central aperture. In one embodiment, distal end 17' of inner rod 16 is generally conically shaped and terminates in a point as illustrated in FIG. 3.

As illustrated in FIGS. 1–3, head 30 of inner rod 16 includes a polygonal cross section to facilitate application of a wrench thereto to rotate inner rod 16 and thread inner rod 16 through self-tapping sleeve 14. In the exemplary embodiment illustrated in FIGS. 1–3, head 30 has a hexagonal cross section. In the alternative embodiment illustrated in FIG. 2, head 30' of inner rod 16 is shaped similar to head 32 of self-tapping sleeve 14 and includes transverse aperture 34'. In this embodiment, inner rod 16 can be actuated as described above with respect to head 32 of self-tapping sleeve 14 to rotate relative to self-tapping sleeve 14 for threading therethrough as illustrated in FIG. 3.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A disassembly apparatus for disassembling a mating taper connection in a pair of interpenetrating pans, a first of the interpenetrating parts including a longitudinal bore having a female taper, a second of the interpenetrating parts including a male taper, said disassembly apparatus comprising:

a sleeve for engaging the first of the interpenetrating parts, said sleeve including a longitudinal bore having internal threads, said sleeve including external self-tapping threads, said sleeve sized whereby the longitudinal bore of the first of the interpenetrating parts accommodates said sleeve, said external self-tapping threads sized whereby rotation of said sleeve with said sleeve positioned in the longitudinal bore of the first of the interpenetrating parts threads the longitudinal bore of the first of the interpenetrating parts and secures said sleeve therein; and an inner rod having external threads, said external threads of said inner rod cooperating with said internal threads of said sleeve whereby rotation of one of said inner rod and said sleeve relative to the other of said inner rod and said sleeve causes axial displacement of said inner rod relative to said sleeve, said inner rod having a distal end.

2. The disassembly apparatus of claim 1, wherein said distal end of said inner rod includes a protrusion extending distally therefrom.

3. The disassembly apparatus of claim 2, wherein said protrusion comprises a conical protrusion.

4. The disassembly apparatus of claim 2, wherein said protrusion includes an apex positioned a distance from a longitudinal axis of said inner rod.

5. The disassembly apparatus of claim 1, wherein said sleeve includes a head having a polygonal cross section.

6. The disassembly apparatus of claim 1, wherein said sleeve includes a head having a transverse aperture formed in said head of said sleeve, said transverse aperture substantially perpendicular to a longitudinal axis of said sleeve.

7. The disassembly apparatus of claim 1, wherein said inner rod includes a head having a polygonal cross section.

8. The disassembly apparatus of claim 1, wherein said inner rod includes a head having a transverse aperture formed in said head of said inner rod, said transverse aperture substantially perpendicular to a longitudinal axis of said inner rod.

9. A disassembly apparatus for disassembling a mating taper connection in a pair of interpenetrating parts, a first of said interpenetrating parts including a longitudinal bore having a female taper, a second of said interpenetrating parts including a male taper, said disassembly apparatus comprising:

a sleeve for engaging the first of said interpenetrating parts, said sleeve including a longitudinal bore having internal threads, said sleeve including affixing means for affixing said sleeve to the first of said interpenetrating parts; and an inner rod having external threads, said external threads of said inner rod cooperating with said internal threads of said sleeve whereby rotation of one of said inner rod and said sleeve relative to the other of said inner rod and said sleeve causes axial displacement of said inner rod relative to said sleeve.

10. The disassembly apparatus of claim 9, wherein said distal end of said inner rod includes a protrusion extending distally therefrom.

11. The disassembly apparatus of claim 10, wherein said protrusion comprises a conical protrusion.

12. The disassembly apparatus of claim 10, wherein said protrusion includes an apex positioned a distance from a longitudinal axis of said inner rod.

13. A disassembly apparatus for disassembling a mating taper connection in a pair of interpenetrating parts, a first of the interpenetrating parts including a longitudinal bore having a female taper and a threaded section, a second of the interpenetrating parts including a male taper, said disassembly apparatus comprising:

a sleeve for engaging the first of the interpenetrating parts, said sleeve including a longitudinal bore having internal threads, said sleeve including external threads, said sleeve sized whereby the longitudinal bore of the first of the interpenetrating parts accommodates said sleeve, said external threads sized whereby rotation of said sleeve with said sleeve positioned in the longitudinal bore of the first of the interpenetrating parts threadedly engages said sleeve in the internal threaded section of the longitudinal bore of the first of the interpenetrating parts; and an inner rod having external threads, said external threads of said inner rod cooperating with said internal threads of said sleeve whereby rotation of one of said inner rod and said sleeve relative to the other of said inner rod and said sleeve causes axial displacement of said inner rod relative to said sleeve, said inner rod having a distal end.

14. The disassembly apparatus of claim 13, wherein said distal end of said inner rod includes a protrusion extending distally therefrom.

15. The disassembly apparatus of claim 14, wherein said protrusion comprises a conical protrusion.

16. The disassembly apparatus of claim 14, wherein said protrusion includes an apex positioned a distance from a longitudinal axis of said inner rod.

* * * * *